United States Patent

Kurosawa et al.

[11] 4,122,189
[45] Oct. 24, 1978

[54] MEDICINE FOR RENAL DISEASES

[75] Inventors: Hidehumi Kurosawa, Toride; Yoshiaki Tanaka, Sakado, both of Japan

[73] Assignee: Kaken Chemical Co., Ltd., Tokyo, Japan

[21] Appl. No.: 779,778

[22] Filed: Mar. 21, 1977

[30] Foreign Application Priority Data

Mar. 31, 1976 [JP] Japan .................. 51-34364

[51] Int. Cl.² .......................................... A61K 31/195
[52] U.S. Cl. .................................................. 424/319
[58] Field of Search .......................... 424/319

[56] References Cited

FOREIGN PATENT DOCUMENTS 45-4,077  2/1970  Japan ........................................ 424/319

Primary Examiner—Frederick E. Waddell
Attorney, Agent, or Firm—Oblon, Fisher, Spivak, McClelland & Maier

[57] ABSTRACT

Methyl methionine sulfonium salts having the formula

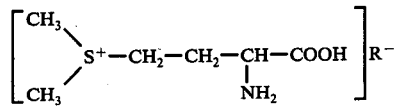

wherein R⁻ represents an inorganic or organic anion are used in remedy for renal diseases and secondary hyper lipoidemia caused by renal diseases.

4 Claims, No Drawings

MEDICINE FOR RENAL DISEASES

BACKGROUND OF THE INVENTION

1. Field of the Invention

The present invention relates to a medicine for renal diseases.

2. Description of the Prior Art

There has not been found perfect therapy for renal diseases. Certain steroids, immunodepressants, nonsteroid anti-inflammatory agents have been used as medicines for nephrotic syndrome. However, these medicines have various disadvantages. For example, the adrenocortical steroids cause slight side-effects of moon face, acne and transient increase of blood pressure and serious side-effects of gastric ulcer such as hematemesis and hematorrhea; infection, mental disorder and pituitary and renal cortex disfunctions.

The immunodepressants cause bone-marrow sanguification disfunction (anemia, leukopenia and blood platelet decrease) nausea, vomiting, liver disfunction, digestive organ disfunction such as stomatitis, skin rash, susceptibility to infections, low γ-globulinemia, herpes zoster, depilation etc..

These diseases are caused by the renal disfunctions.

The non-steroid anti-inflammatory agents cause side-effects of digestive organ disfunction, latent infections and aggravation of infections, etc..

The inventors have studied on medicines for renal diseases and have found that methyl methionine sulfonium salts are remarkably effective as medicines for renal disease nephrotic syndiome characterized by excessive urinary protein.

SUMMARY OF THE INVENTION

It is an object of the present invention to provide a medicine for renal diseases and secondary hyper lipoidemia caused by renal diseases.

The foregoing and other objects of the present invention have been attained by providing a medicine for renal diseases and secondary hyper lipoidemia caused by renal diseases which comprises methyl methionine sulfonium salt having the formula

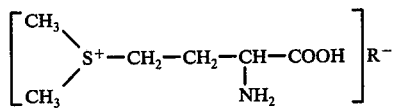

wherein $R^-$ represents an inorganic or organic anion as an active ingredient.

DETAILED DESCRIPTION OF THE PREFERRED EMBODIMENTS

The active ingredients of methyl methionine sulfonium salts used in the invention are the known compounds and have been used for gastro ulcer, duodenal ulcer, gastritis and hepatitis and can be produced by the process disclosed in Japanese Patent Publication No. 4757/1962 and the like.

The methyl methionine sulfonium salts can have the inorganic or organic anion.

Suitable inorganic anions include $Cl^-$, $Br^-$, $I^-$, $SO_4^{--}$ etc. and suitable organic anions include carboxylic acid ions such as $CH_3COO^-$ and

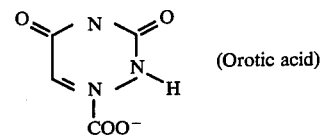

(Orotic acid)

and sulfonic acid ions such as $C_6H_{11}NHSO_3^-$ (Cyclamic acid).

The optimum anions include $Cl^-$ and $I^-$.

Methyl methionine sulfonium chloride is especially preferable because of no hypersensity and economical reason.

The medicines for renal diseases of methyl methionine sulfonium salts can be applied by oral dose, intravenous injection and in the other conventional manner.

The dose of the methyl methionine sulfonium salt is dependent upon the kind and the severeness of renal diseases and is remarkably high, namely more than 200 mg usually 1000 to 2000 mg per one day in the oral dose for adult.

The methyl methionine sulfonium salts of the invention can be used in various forms such as tablet, capsule, injectable and the other medical forms.

The active ingredients of methyl methionine sulfonium salts can be applied together with the other medicines such as antibiotics, steroids, immunodepressants, diuretics, nonsteroid anti-inflammatory agents, etc..

The characteristics of the methyl methionine sulfonium salts are effective for excessive urinary protein, hypercholesterolemia, and cause less side-effects and especially no serious side-effect. Accordingly, the methyl methionine sulfonium salts are remarkably effective for renal diseases for a long term therapy with or without the other medicine such as steroids and immunodepressants.

EXPERIMENT 1

Clinical Test

Methyl methionine sulfonium chloride was administrated to 45 patients having excessive urinary protein at a dose of 150 to 1800 mg/day with or without the other medicines shown in Table 1, singly or in combination with the additional medicines shown below.

When used in combination, the additional medicines were dosed in the amount usual for each of such additional medicines.

The amount of urine protein was measured for the clinical tests. The elimination or remarkable degree of reduction of urine protein was considered to be effective. As the result, 32 cases among 45 patients were effective and the side-effect was only one diarrhoea.

The non-steroid anti-inflammatory agents such as Ibuprofen, Indomethacin, Azapropazone, and steroids such as Predonizolone and antibiotics such as Cephalexin, methyl chlorophenyl iso-oxazolyl penicillin were used as the additional medicines.

Table 1

| No. | Age | Sex | Disease | Dose (mg/day) | Term (day) | Urine protein Before | Urine protein After | Additional medicine |
|---|---|---|---|---|---|---|---|---|
| 1 | 32 | ♀ | R-1 | 1200 | 18 | ± | − | Add. |
| 2 | 22 | ♀ | R-2 | 1000 | 84 | ++ | + | |
| 3 | 56 | ♀ | R-3 | 1200 | 14 | + | − | |
| 4 | 10 | ♂ | R-4 | 600 | 21 | + | − | Add. |
| 5 | 49 | ♀ | R-5 | 1200 | 147 | + | ± | Add. |
| 6 | 35 | ♂ | R-6 | 300 | 70 | ± | − | |
| 7 | 48 | ♀ | R-7 | 1200 | 329 | ++ | + | Add. |

Table 1-continued

| No. | Age | Sex | Disease | Dose (mg/day) | Term (day) | Urine protein Before | Urine protein After | Additional medicine |
|---|---|---|---|---|---|---|---|---|
| 8 | 26 | ♀ | R-8 | 300 | 231 | ± | — | |
| 9 | 15 | ♀ | R-9 | 150 | 14 | +++ | + | |
| 10 | 35 | ♀ | R-10 | 1200 | 14 | ++ | + | Add. |
| 11 | 55 | ♂ | R-11 | 1200 | 371 | ++ | + | Add. |
| 12 | 11 | ♂ | R-12 | 900 | 21 | ± | — | |
| 13 | 68 | ♀ | R-13 | 300 | 42 | ++ | — | Add. |
| 14 | 61 | ♂ | R-14 | 300 | 14 | + | — | Add. |
| 15 | 75 | ♂ | R-15 | 300 | 119 | +++ | + | |
| 16 | 76 | ♂ | R-16 | 300 | 35 | ± | — | |
| 17 | 39 | ♀ | R-17 | 300 | 42 | ++ | — | Add. |
| 18 | 53 | ♀ | R-18 | 300 | 49 | ± | — | |
| 19 | 26 | ♀ | R-19 | 1200 | 14 | ± | — | |
| 20 | 72 | ♀ | R-20 | 1200 | 54 | ± | — | |
| 21 | 23 | ♀ | R-21 | 1200 | 98 | ++ | — | Add. |
| 22 | 22 | ♀ | R-22 | 750 | 42 | + | — | |
| 23 | 23 | ♂ | R-23 | 750 | 24 | ++ | + | |
| 24 | 18 | ♀ | R-24 | 750 | 90 | ++ | + | |
| 25 | 27 | ♂ | R-25 | 750 | 28 | ++ | + | |
| 26 | 25 | ♂ | R-26 | 600 | 35 | ± | — | |
| 27 | 21 | ♀ | R-27 | 750 | 29 | ± | — | |
| 28 | 37 | ♀ | R-28 | 1800 | 42 | + | — | Add. |
| 29 | 27 | ♂ | R-29 | 1800 | 140 | +++ | ++ | Add. |
| 30 | 23 | ♂ | R-30 | 1800 | 112 | + | — | |
| 31 | 22 | ♂ | R-31 | 1800 | 196 | ++ | + | Add. |
| 32 | 53 | ♀ | R-32 | 1800 | 70 | + | — | |

R-1: subacute nephritis
R-2: nephritis
R-3: right nephritis
R-4: child nephritis
R-5: gout nephritis
R-6: pyelonephritis
R-7: pyelitis
R-8: chronic pyelonephritis
R-9: pyelitis
R-10: wandering right kidney
R-11: renal sclerosis
R-12: excessive urinary protein
R-13: bladder tumor
R-14: prostatic gland hypertrophy
R-15: "
R-16: "
R-17: pyelitis
R-18: light nephritis
R-19: wandering right kidney
R-20: right pyelitis
R-21: nephrotic syndrome
R-22: chronic nephritis
R-23: "
R-24: nephrotic syndrome
R-25: "
R-26: "
R-27: "
R-28: acute glomerulone phiritis
R-29: nephrotic syndrome
R-30: "
R-31: "
R-32: "

EXPERIMENT 2

Therapy for Aminonucleoside nephrose

SD type male rats (weight about 100 g) were fed in each individual room of a metabolism cage under the free water and feed supply.

The rats were classified as the normal group for eight rats, the renal disease group for eight rats and the therapy group for eight rats.

0.3% Aminoucleoside aqueous solution (hereinafter referring to as AN) was administrated by intramuscular injection at a dose of 0.3 ml per 100 g of the rat.

The administration was continued from the 1st day to the 14th day at one time per day.

For the therapy group, methyl methionine sulfonium chloride was administrated by the oral dose at a dose of 1000 mg/kg (in a form of 1.0 ml per 100 g of the weight of rat) at one time per day for 10 days with AN from 5th day when the increase of the amount of urine protein was found.

The results of urine and blood biochemical observations are shown in Table 2 and Table 3.

The data in Tables are average value for eight rats in each group.

The difference between the renal disease group and the therapy group was significant. The symbol * means the existence of significant difference in 5% of the level of significance and the symbol (*) means the existence of significant difference in 5 to 1% of the level of significance. The symbol — means non-significant difference.

Table 2

| | Normal group | Renal disease group | Therapy group | Significant difference |
|---|---|---|---|---|
| Weight (g) | 180 | 196 | 176 | * |
| Urine amount (ml/day) | 9.4 | 8.5 | 6.9 | (*) |
| Urine pH | 6.7 | 6.5 | 6.2 | (*) |
| Urine protein (g/dl) | 0.6 | 5.2 | 4.0 | * |
| Urine protein (mg/day) | 54 | 441 | 294 | * |
| Urine albumin (g/dl) | 0.1 | 2.4 | 1.6 | * |
| Urine albumin (mg/day) | 6.6 | 196 | 106 | * |
| Urine Na (m Eq/l) | 160 | 54 | 109 | * |
| Urine K (m Eq/l) | 230 | 204 | 210 | — |

Table 3

| Serum biochemical Test | Normal group | Renal disease group | Therapy group | Significant difference |
|---|---|---|---|---|
| Total protein (g/dl) | 6.48 | 3.60 | 4.47 | * |
| Albumin (g/dl) | 2.60 | 0.49 | 1.25 | * |
| Albumin/Globulin ratio | 0.68 | 0.16 | 0.41 | * |
| Cholesterol (mg/dl) | 84.3 | 277 | 149 | * |
| Glycose (mg/dl) | 169 | 135 | 138 | — |
| Urea nitrogen (mg/dl) | 25.2 | 44.8 | 23.8 | * |
| $Na^+$ (m Eq/l) | 134 | 135 | 134 | — |
| $K^+$ (m Eq/l) | 5.1 | 5.4 | 5.6 | — |

The results in Tables 2 and 3 show that the methyl methionine sulfonium salt of the invention is effective for the renal disease.

EXPERIMENT 3

Therapy for hetero antikidney serum nephritis

Wister type male rats (weight of about 180 g) were classified as the normal group, the renal disease group and the therapy group(dose of 1000 mg/kg per day of methyl methionine sulfonium chloride) and were fed in each individual room of a metabolism cage.

Antikidney serum (rabbit) prepared in accordance with the Heymann method was intravenously injected into tail vein at a dose of 0.5 ml per 100 g of rat at one time per day.

The methyl methionine sulfonium chloride was administrated by oral dose for 9 days from one day before the injection.

The results are shown in Table 3.

In Table 3, the symbols for tissue observation mean the following conditions of tissues.

A: Proliferation of polymorphs of glomeruli
B: Thrombus formation
C: Thickning of the basement membrane of the glomerular capillaries
D: Obliteration of the glomerular capillary loops
E: Anemia
F: Exudate in Bowman's subcapsule space
G: Thickning of Bowman's capsule
H: Crescent formation of glomeruli I: Proteinaeous fluid in the tubli
J: Swelling of tublar epithelium
K: Proliferation of interstitial tissue cells In Table 4, the degree of lesions were rated as follows:

0: no lesion of tissue is found;
0.5: slight lesion of tissue is found;
1: clear sporadic or slight lesion of tissue is found;
3: inflamed or clear lesion of tissue is found.

The average of ratings for 5 rats in each group is shown.

The level of significance was considered as the same with those of Table 1.

Table 4

|  | Normal group | Renal disease group | Therapy group | Significance |
|---|---|---|---|---|
| Urine urea (mg/day) | 6.3 | 121 | 104 | — |
| Urea nitrogen in blood (mg/dl) | 23 | 25 | 24 | — |
| Observation of tissue A | 0 | 1.4 | 0.5 | (*) |
| " B | 0 | 1.1 | 0.1 | * |
| " C | 0 | 1.7 | 0.4 | * |
| " D | 0 | 1.7 | 0.3 | * |
| " E | 0 | 2.2 | 0.1 | * |
| " F | 0 | 0 | 0 | — |
| " G | 0 | 1.1 | 0 | * |
| " H | 0 | 1.1 | 0 | * |
| " I | 0.6 | 1.8 | 0.8 | (*) |
| " J | 0.5 | 1.6 | 1.3 | — |
| " K | 0 | 0.2 | 0.3 | — |

The results in Table 4 show that the methyl methionine sulfonium salt of the invention is effective for the renal disease.

EXPERIMENT 4

Toxicity Test

Methyl methionine sulfonium chloride was dissolved in each distilled water at various concentration to give 0.2 ml per 10 g of mouse.

The test was carried out by the oral dose and the intraperitoneal injection of each solution in 10 ddY type male mice and 10 ddY femal mice. The results after 72 hours from the administration were observed. Probit analysis was used for statistical treatment of mortality.

The results are shown in Table 4. The low toxicity of methyl methionine sulfonium chloride was found.

Table 5

| Mouse | Dose | $LD_{50}$(mg/kg) |
|---|---|---|
| male | oral dose | 11920 |
| female | " | 11255 |
| male | Intraperitoneal injection | 8139 |
| female | " | 7910 |

Composition

A 500 g of methyl methionine sulfonium chloride was uniformly admixed with 100 g of aluminum silicate and 350 g of corn starch (60 mesh sieve pass).

The mixture was charged into a kneader and 670 ml of 3% ethanol solution of hydroxypropyl cellulose was added into it, and the mixture was kneaded and was granulated by passing through a 16 mesh sieve and was dried by passing air at 45° C.

After drying the granules, the granules were passed through a 16 mesh sieve and was admixed with 16 g of magnesium stearate and 20 g of talc.

The mixture was treated by the tablet machine to form tablets having a diameter of 8 mm and a weight of 200 mg.

What is claimed is:

1. A method for treating a human exhibiting at least one of the disorders of excessive urinary protein and secondary hyper lipoidemia due to a renal disease which comprises internally administering to said human a methyl methionine sulfonium salt having the formula

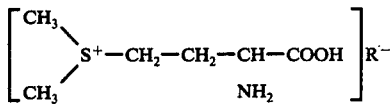

where $R^-$ represents the chloride or iodide anion in an amount effective to produce at least one of anti-excessive urinary protein therapy and anti-hyper lipoidemia therapy during the course of said renal diseases.

2. The method of claim 1 wherein the administration of the methionine salt is oral and in a dosage of 200 to 2000 mg per day.

3. A method for treating a human exhibiting at least one of the disorders of excessive urinary protein and secondary hyper lipoidemia due to a renal disease which comprises internally administering to said human a methyl methionine sulfonium salt having the formula

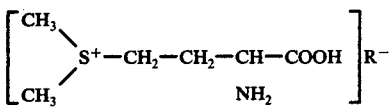

where $R^-$ represents a pharmaceutically acceptable anion in an amount effective to produce at least one of anti-excessive urinary protein therapy and anti-hyper lipoidemia therapy during the course of said renal diseases.

4. The process of claim 1 wherein the administration is in an amount effective to produce anti-hyper lipoidemia therapy.

* * * * *